United States Patent [19]

Lasic et al.

[11] Patent Number: 5,185,154

[45] Date of Patent: Feb. 9, 1993

[54] METHOD FOR INSTANT PREPARATION OF A DRUG CONTAINING LARGE UNILAMELLAR VESICLES

[75] Inventors: Danilo D. Lasic; Andrej Belic, both of Sunnyvale, Calif.

[73] Assignee: Liposome Technology, Inc., Menlo Park, Calif.

[21] Appl. No.: 486,131

[22] Filed: Feb. 28, 1990

Related U.S. Application Data

[62] Division of Ser. No. 305,348, Feb. 2, 1989, abandoned.

[51] Int. Cl.⁵ .............................................. A61K 37/22
[52] U.S. Cl. ...................................... 424/450; 264/4.6; 424/1.1; 427/2; 427/3; 428/402; 428/402.2
[58] Field of Search .................. 424/450, 1.1; 264/4.6; 427/2, 3; 428/402, 402.2

[56] References Cited

U.S. PATENT DOCUMENTS 5,023,087  6/1991  Yau-Young .......................... 424/450

OTHER PUBLICATIONS

Biochem. Biophys. Acta 896:117 (1987).
J. Colloid and Inter. Sci. 124(2):428 (1988).
J. Theor. Biol. 124:35 (1987).
J. Amer. Chem. Soc. 110:970 (1988).
Biochemistry 25(10):2812 (1986).
Biochemistry 25:7477 (1986).
Biochem. Biophys. Acta 816:1 (1985).
J. Mol. Biol. 8:660 (1964).

*Primary Examiner*—Thurman K. Page
*Assistant Examiner*—Robert H. Harrison

[57] ABSTRACT

This invention describes a simple, fast, reproducible economic, and convenient method of preparation of very large unilamellar liposome vesicles of uniform size distribution. The populations of these vesicles are homogeneous and suitable for encapsulation of water and lipid soluble compounds.

16 Claims, No Drawings

METHOD FOR INSTANT PREPARATION OF A DRUG CONTAINING LARGE UNILAMELLAR VESICLES

This application is a division of application Ser. No. 07/305,348, which was filed on Feb. 2, 1989, abandoned.

BACKGROUND OF THE INVENTION

1. Field of the Invention

This invention concerns a novel method for the preparation of large unilamellar liposomal vesicles. The method is fast, simple, economical, reproducible and convenient and avoids lengthy and harsh chemical and physical conditions and procedures which are detrimental to the lipids and/or drugs or substances to be encapsulated therein.

2. Related Disclosures

Liposomes are now recognized as a drug delivery system which can improve the therapeutic activity and safety of a wide range of compounds. A prerequisite to the successful development and commercialization of liposome products is the capability to scale up production methods in compliance with currently accepted good manufacturing practices, at acceptable cost and using processes which provide the high degree of reproducibility required for finished pharmaceuticals and are void of conditions and manipulations which would destroy, modify or otherwise deactivate these pharmaceuticals.

A number of review, for example *Liposomes as Drug Carriers*, Wiley and Sons, New York (1988), *Liposomes from Biophysics to Therapeutics*, Marcel Dekker, New York (1987) have described studies of liposome production methodology and properties, their use as carriers for drugs and interaction with a variety of cell types and pointed out the fact that liposome behavior can vary substantially with certain formulation variables, most notably it would depend on chemical composition, size, surface charge, and drug payload. Therefore, it is desirable to have available a method to form liposomes using processes which control these variables.

Liposomes are small closed spherical structures formed from phospholipids (PLs) in aqueous solutions. Liposomes which are formed by single lipid bilayer are called unilamellar vesicles; those formed by multiple bilayers are called multilamellar vesicles (MLVs). Each liposomal layer is formed by a single phospholipid bilayer which separates internal and external solutions and which bilayer is able to entrap the solvent or drug solute in liposome interior or in the space between two liposomal bilayers in case of MLVs. Unilamellar vesicles may be small liposomes (SUVs) or large liposomes (LUVs).

SUVs and LUVs are important in the studies of membranes, membrane proteins, and as delivery vehicles for drugs and genetic material into cells, and many different methods for their preparation exist. However, most of these methods are time consuming, uneconomical, not reproducible, and require relatively demanding laboratory equipment. These methods involve the exposure of PLs and substance to be encapsulated in liposomes to physical stresses such as sonication, or high hydrostatic pressures and/or exposure to a severe chemical environment such as organic solvents, detergents, low/high pH, all of which may harm these sensitive substances.

Thus, a simple, quick, economical, reproducible and harmless method for vesicle preparation is still being searched for and would be convenient.

Large unilamellar vesicles (LUVs) provide a number of important advantages as compared to MLVs including high encapsulation of water soluble drugs, economy of lipid and reproducible drug release rates. However, LUVs are perhaps the most difficult type of liposomes to produce. "Large" in the context of liposomes usually means any structure larger than 0.1 micron; thus large unilamellar vesicles refers to vesicles bounded by a single bilayer membrane that are above 0.1 micron in diameter.

Two primary methods are used to produce LUVs. One involves the detergent dialysis, the other involves the formation of a water-in-oil emulsion. A number of other techniques for producing LUVs have been reported including freeze-thaw cycling, *J. Biol. Chem.*, 252:7384 (1977), slow swelling in nonelectrolytes, *J. Cell Physiol.* 73:49 (1969), dehydration followed by rehydration, *BBA:* 816:1 (1985) and dilution or dialysis of lipids in the presence of chaotropic ions *Biochemistry*, 22:855 (1983). All these methods, however, show various disadvantages and may not be suitable for large scale pharmaceutical preparations.

Removal of detergent molecules from aqueous dispersions of phospholipid/detergent mixed micelles represents one way for producing liposomes, in particular LUVs. As the detergent is removed, the micelles become progressively richer in phospholipid and finally coalesce to form closed, single bilayer vesicles. Shortcomings of this approach include leakage and dilution of the drug during liposome formation, the danger of drug modification or deactivation by detergent, high cost and quality control of the detergent and the difficulty of removing the last traces of the detergent once liposomes have formed. Three major methods of detergent removal appropriate for this purpose of forming liposomes have been described, namely dialysis, column chromatography and by using Bio-Beads.

Detergent dialysis as a method for liposome preparation is described in *J. Biol. Chem.*, 246:5477 (1971). Detergents commonly used for this purpose include the bile salts and octylglucoside. During dialysis, liposomes are formed in the 0.003–0.2 micron diameter range within a few hours. The procedure requires the use of continuous pumping of buffer or several changes of dialysate if the dialysis is performed in the dialysis bags.

The formation of 100 nm single layered phospholipid vesicles LUVs) during removal of detergent deoxycholate by column chromatography has been reported in *Biochemistry*, 18:145 (1979). The method calls for mixing phospholipid, in the form of either small sonicated vesicles or a dry lipid film, with deoxycholate at a molar ratio of 1:2, respectively. Subsequent removal of the detergent during passage of the dispersion over a Sephadex G-25 column results in the formation of uniform 100 nm vesicles that are readily separable from small sonicated vesicles. Again, this is a lengthy and laborious process of preparing LUVs.

Another method for forming reconstituted membranes reported in *J. Eur. Biochem.*, 75:4194 (1978) may also be applicable to LUVs preparation. The system involves the removal of a nonionic detergent, Triton X-100, from detergent/phospholipid micellar suspensions. This method is based on the ability of Bio-Beads SM-2 to absorb Triton X-100 rapidly and selectively. Following absorption of the detergent, the beads are removed by filtration. The final particle size appears to depend on the conditions used including lipid composition, buffer composition, temperature, and, most critically, the amount and detergent-binding activity of the beads themselves. While this method seems to be fastest of all above, it still includes impractical manipulation such as handling the beads and filtration not to mention possible contamination of sample with impurities which are often introduced by the use of nonrecrystallized detergent.

LUVs can also be prepared by reverse phase evaporation technique (REV), by forming a water-in-oil emulsion of phospholipids and buffer in presence of an excess organic phase followed by removal of the organic phase under reduced pressure. REV method is disclosed in U.S. Pat. No. 4,235,871. The two phases are usually emulsified by sonification or by other mechanical means. Removal of the organic solvent under vacuum causes the phospholipid-coated droplets of water to coalesce and eventually form a viscous gel. Removal of the final traces of solvent under high vacuum or mechanical disruption, such as vortexing, results in the collapse of the gel into a smooth, nonviscous suspension of LUVs. With some lipid compositions, the transition from emulsion to LUV suspension is so rapid that the intermediate gel phase appears not to form. This method has gained widespread use for liposome formulation which require high encapsulation of a water soluble drug. Drug solute entrapment efficiencies up to 65% were reported.

To prepare REV-type liposomes, the phospholipids are first dissolved in an organic solvent such as diethylether, isopropylether, or their mixtures. The aqueous phase containing the material to be entrapped is added directly to the phospholipid-solvent mixture forming a two-phase system. The two phases are sonicated for a few minutes forming the water-in-oil emulsion, and the organic phase is carefully removed under a partial vacuum. The pressure is usually maintained at about 500 mm Hg for the removal of the bulk of the organic phase (using a nitrogen gas bleed to regulate the vacuum) and then lowered cautiously to complete solvent stripping. Removal of the last traces of solvent transforms the gel into LUVs. Such LUVs have been used to encapsulate both small and large chemical molecules. Biologically active macromolecules such as RNA and various enzymes have been encapsulated without loss of activity.

The principal disadvantage of the REV and other methods described supra is the exposure of the material to be encapsulated in liposomes to organic solvents and to mechanical agitation, both of which can lead to denaturation of proteins, introduction of nicks into nucleic acid strands, modification of chemical entities, and to overall change in biological activity.

Moreover, as is apparent from the above description, all other known and available methods for preparation of LUV's are lengthy, laborious and involve the use of strong chemicals such as for example detergents and organic solvents in combination with procedures for their removal, such as dialysis, column chromatography, biobeads, absorption, filtration, freeze drying, etc. The other methods use intrusive procedures such as REV technique, and require the presence of a very strong organic solvents such as for example, diethylether, isopropylether, trichlorotrifluoromethane, etc.

Disadvantages of such procedures and treatments are apparent since the chemically sensitive molecules such as many pharmaceutical drugs, can hardly withstand an exposure to detergents or organic solvents or to treatment using mechanical agitation, sonication, high shear mixing accompanied unavoidably with high temperatures, filtration, dialysis, high pressure, etc. Treatments using the above means can alter the chemical entity of the drug, often irreversibly and thus change its intended therapeutical use.

Thus it would be highly advantageous to have a simple method for preparation of LUVs which would allow avoidance of both strong chemicals and harsh mechanical procedures.

It has been shown previously that in the aqueous solutions, phospholipid molecules form self closed spherical structures where one or several phospholipid bilayers entrap part of the solvent in its/their interior, and that MLVs are formed spontaneously when dry films composed of neutral phospholipid(s) are hydrated and swollen in excess water by gentle shaking *J. Mol. Biol.*, 8:660 (1964). In contrast to the finite swelling behavior of uncharged neutral films, charged phospholipid films exhibit infinite swelling in excess of water, and the spontaneous formation of heterogeneous populations of vesicles. By using similar procedures, fairly homogeneous preparations of SUVs have been reported, *BBA*, 896:117 (1987), with however, unavoidably large losses of phospholipids. Moreover, in general, SUVs are not very suitable for economical encapsulation of expensive water soluble pharmaceutical drugs because of their small internal volume.

It is, therefore, a primary object of this invention to provide a simple, fast, economical, reproducible and convenient method for preparation of very large liposomes, in the form of large unilamellar vesicles primarily of around 1 micron size.

A very limited scope of this invention was published by inventors in *JACS*, 110:970 (1988) on Feb. 3, 1988.

SUMMARY

One aspect of this invention is to prepare a substantially homogeneous population of large unilamellar liposomal vesicles of uniform size.

The other aspect of this invention is the simple, fast, economical, reproducible, and convenient process of preparing liposomal LUVs where the size of the LUVs is controlled by the topography of the support template surface on which the lipid film is deposited prior to water reconstitution.

DETAILED DESCRIPTION OF THE INVENTION

The current invention circumvents all above listed disadvantages and provides the method for instant and spontaneous formation of homogeneous preparation of LUVs by adding the water or aqueous solvent to the dry phospholipid film deposited on a specially prepared surface, such as for example etched silicon wafers of which the topography forms a template determining the size of LUVs. The surface of the template determines the size of the formed LUVs. The formation of multilamellar vesicles is prevented by the use of charged phospholipids or neutral phospholipids which are slightly doped from 1 to 5 wt. %, or possibly more, with charged phospholipid(s) or other charged surfactant. The combination of both above assures almost homogeneous size population of LUVs.

In the practice of the current invention, used phospholipids (PL) are either neutral such as egg yolk lecithin (EYL) or charged phospholipids, such as phosphatidylcholine (PC), phosphatidylglycerol (PG), phosphatidic acid (PA), phosphatidyl ethanolamine (PE), phosphatidylseriene (PS), phosphatidylinositol (PI), cardiolipin and others which may be suitable for this purpose as long as they are charged or may be charged. Phospholipids may be fully saturated or partially hydrogenated and may be naturally occurring or synthetic. Phospholipids' aliphatic chains are preferably at least about 12 atoms in length, preferably between 15 and 24 atoms long.

The lipids used to form LUVs according to this invention must be charged. Thus, the lipids used are either charged naturally or when neutral, they must be doped with charged phospholipids or surfactants.

Neutral phospholipids, such as EYL are charged by spiking or doping with small amount of any other charged phospholipid or of detergent, such as anionic or cationic detergent, examples being sodium dodecylsulfate, oleic acid, soaps or preferably cationic detergent cetyltrimethylammonium bromide (CTAB). The mixture of EYL and the detergent is dissolved and mixed in an organic solvent, such as halogenated hydrocarbons and aliphatic alcohols, preferably in a mixture of trichloromethane/methanol in amounts from 0.1 to 3 mg of PL, with from 0.5 to 10 wt. % of the detergent and 1–10 ml of organic solvent mixture, preferably in amounts 0.5–1 mg of PL, 1.5–5 wt. % of the detergent, and 3 ml of the solvent mixture. For charged PL, it is not necessary to use any detergent and these PLs are directly mixed with the solvent in the same amount range.

The above obtained mixture is deposited on the support template surface. The template can be any natural or artificially made rough surface material such as ceramic or nonceramic microfilters, diffraction grids, CD recorded disks, turn table records, sanding paper and such others, made of polyethylene, plastics, ceramics, silicon, metals, glass, wood, fibers and such others, made of manufactured by method such as cutting, sanding, etching, sputtering or any other method suitable and available to make such templated surfaces. Preferably, the support template surface is an etched silicon wafer. The etched silicon wafer or other type of support template can be prepared by any process generally acceptable in electronic, micro- electronic, or other industry. The technological steps which lead to the preparation of the silicon wafer with the template surface may include the following: cleaning of silicon wafer, oxidation of silicon in the mixture of hydrogen and oxygen, dehydration bake of the surface, application of photoresist, baking of the photoresist layer, aligning of the template mask to the wafer and exposure under UV light, development of the photoresist image, baking of the photoresist image, etching of the silicon dioxide layer, removing of the photoresist, ion implantation and high temperature activation. For example, the template for LUV formation can be prepared as 4 inch silicon wafer with the top layer of silicon dioxide where the top layer is patterned with a special template mask, that is, certain areas of silicon dioxide were etched away to expose silicon. Exposed silicon area is selectively doped with boron or other metal. The vertical topography of wafer prepared by the above mentioned procedure is for instance 0.1–1.0 um with the horizontal pattern of silicon and/or silicon dioxide 3–10 um in dimension.

The obtained wafer is cleaned in hot acid peroxide mixture, preferably $H_2SO_4H_2O_2$, dip etched in 10/1 HF, rinsed in deionized water and dried. The methods described above are known in the art and described in, for instance, *The Physics of Microfabrications*, Plenum Press, New York, (1982).

The same or similar preparation techniques can be utilized for preparation of the micropatterned substrate template with different film types on different substrate material.

Silicon material of different type, orientation, and resistivity can be used. Other materials such as silicon dioxide, silicon nitride, aluminum, gold, tantalum, etc. can be advantageously used. Particularly suitable choice for substrate material is ceramic, metal or plastics such as polyethylene.

The thickness of thin film material or the depth of micropatterning is anywhere from 0.1 to several microns.

Micropattern for preparation of support template surface that would enable formation of large uniform vesicles consists of small areas of regular shape, such as indentions, pores, holes, etc., which are repeated at a uniform distance across the entire substrate. Micropattern form the matrix for sizing LUVs.

The dimensions of the regular shape are as small as possible. For instance the pattern can be a) square chess board pattern; b) rectangular stripe pattern; or c) isolate regular shapes.

The phospholipid mixture, deposited on the rough support template surface, is dried into a phospholipid film by any means generally used in the laboratory and suitable for drying aqueous and organic solvents, such as for example, drying in a rotary evaporator, under nitrogen flow or in vacuum and followed by high vacuum evacuation. The preferred methods for drying are those where there is a slow evaporation at reduced pressure with no shaking, rotating, or other mechanical disturbance so that the lipid film deposits evenly, at mild temperature from 10°–40° C., preferably at 20°–24° C., at pressures from 300–800 mm Hg, preferably at around 600 mm Hg. The alternative method for the application of phospholipid mixture on the silicon wafer with a template surface is by spinning of the wafer on the spinner similar or identical to the ones which are used for applying of the photoresist in the semiconductor industry. The spinning parameters such as spinning speed between 300–3,000, preferably 1,000 rpm, and spinning time between 0.5 to 20 minutes, preferably three minutes, precisely determine the thickness of the phospholipid film. The above method gives a very uniform film and traces of the remaining solvent can be removed by vacuum drying.

After the solvent evaporation, the deposited phospholipid film is dried for 5–48 hours, preferably overnight under a vacuum, preferably at vacuum of about from $10^{-2}$ to $10^{-3}$ mm Hg.

To form liposomes as LUVs of around 1 micron size, 0.5–10 ml, preferably at vacuum of about from $10^{-2}$ to $10^{-3}$ mm Hg. or other compound to be encapsulated in LUVs, is added to the deposited lipid film on the template surface. By this simple act of water addition, the LUVs of uniform size are formed instantly without use of any mechanical procedure. Thus, no shaking, filtering, sonication, extruding, evaporating, column separation, dialysis, lyophilizing, using absorbers, emulsifying or other intrusive procedures are necessary for liposome formation and for drug encapsulation in LUVs.

The aqueous medium is typically a buffered aqueous solution having a pH between about 6.0 and 7.5, and usually containing the water-soluble pharmaceutical agent or compound which is to be encapsulated in the liposomes.

The size of the vesicles (LUVs) formed by the process of this invention depends on and is determined by the size of indentions, pores, holes, openings, etc. on the template surface and on its surface topography.

The homogeneity of the LUVs is assured by preventing the formation of other structures than LUVs, such as MLVs or SUVs. The formation of MLVs is prevented by inducing the surface charges on the lipid bilayers. The uniformity and smoothness of the deposited film minimizes the formation of SUVs. The surface charge of the bilayer can be achieved by either using the EYL doped with the detergent, such as CTAB, or any other charged phospholipid, or with using naturally charged phospholipids such as PS, PI, PG, and others. The proper surface charge may or may not require the change of pH. The inconvenience and harmful effect of introducing detergent into the bilayer can be bypassed by doping EYL with ionic PLs instead of the detergent CTAB.

The homogeneity and the size of the obtained LUVs was determined by freeze fracture electron microscopy. Video enhanced phase contrast optical microscopy was used to investigate the contamination of LUVs with MLVs, giant vesicles or other phospholipid colloid particles. Gel chromatography, electron microscopy, and $^1$H NMR were used to determine the contamination of LUVs with SUVs.

The current process is not only fast and simple but it is also conveniently economical in that the losses of PL due to incomplete absorption of the lipid mixture on the rough surface or on the wafer are very small and in no way are larger than in the case where unmodified glass flasks are used as a support. By dissolving the lipid film with aqueous solvent in this manner, the vast majority of phospholipid molecules is recover and they are reformed into LUVs.

The reproducibility of the method of this invention is determined by repeated use of the support template surface for preparation of several batches of LUVs. For that purpose, after its use, the wafer-bottomed Erlenmeyer flask was washed with the mixture of organic solvent and alcohol such as $CHCl_3/CH_3OH$ (3:1), rinsed with distilled water, dried, and rinsed in the same manner several times to remove any remnants of phospholipids and/or drugs. The rigorous cleaning, however, is preferred which requires, exactly as is the case with normal glassware, the oxidation of any possible absorbates in concentrated $H_2SO_4H_2O_2$ (1/1) mixture followed by rinsing with deionized water. Following this approach, several different preparations yielded, the same size populations of LUVs.

The silicon wafer as a template surface can be utilized in several different ways: (i) it can be made a bottom of an Erlenmeyer flask with the cut off bottom part where the diameter of the opening matches the diameter of silicon wafer and the latter can be glued on the remaining part of the Erlenmeyer flask as a bottom; (ii) it can be put into a Petri dish for the drying processes of the lipid film and hydration; or (iii) it can be used on a spinner and after drying, the wafer phospholipid film can be hydrated in a Petri dish or beaker.

The advantages of this method are its extreme simplicity, rapidity, reproducibility, and avoidance of all potentially harmful treatments and chemicals. In addition, the LUVs which are formed are of homogeneous, larger size than vesicles prepared by most other techniques and are thus able to incorporate larger amounts of drugs inside liposomes. This property and their quick and harmless preparation make LUVs prepared by the method of this invention extremely suitable for the encapsulation of pharmaceutical drugs and genetic materials which are in particular very sensitive to harsh chemical or physical treatments.

Any pharmaceutical or nonpharmaceutical drug, agent, compound, substance, genetic or other material which is soluble in water or in lipids can be advantageously encapsulated in the LUVs formed by the process of this invention without the danger of being chemically modified, disactivated or destroyed by the chemicals or procedures used in formation of liposomes by methods other than that of this invention.

The pharmaceutical agent may be any drug, hormone, peptide, vitamin, or other pharmaceutical agent which is relatively soluble in the aqueous medium and which can be released from liposomes at a controlled rate, when the liposomes are administered parenterally, topically, by inhalation, or other route. The controlled release may be by passage of the agent through the liposomal membrane, in the case of a liposome-permeable agent, or by liposome breakdown, in the case of a liposome-impermeable drug. Representative water-soluble drugs include terbutaline, albuterol, atropine, methyl, cromyln sodium, propranolol, flunisolide, ibuprofen, gentamycin, tobermycin, pentamidine, penicillin, theophylline, bleomycin, etoposide, captopril, n-acetyl cysteine, verapamil, fluorouracil, iodouridine, trifluorouridine, vidarabine, azidothyidine, ribavirin, phosphonoformate, phosphonoacetate, acyclovir, cemetidine, naphazoline, lodoxamide, naproxen, ibuprofen, and phenylepinephrine, exemplary of relatively small compounds that may be diffusable through liposome bilayer membranes. Suitable water-soluble, liposome-impermeable compounds include peptides, hormones, enzymes, enzyme inhibitors, apolipoproteins, and higher molecular weight carbohydrates. Representative compounds in this class include calcitonin, atriopeptin, alpha1 antitrypsin, interferon, oxyteocin, vasopressin, insulin, interleukin-2, superoxide dismutase, tissue plasminogen activator, plasma factor 8, epidermal growth factor, tumor necrosis factor, lung surfactant protein, and lipocortin. The concentration of drug in the aqueous medium is preferably that which is desired in the encapsulated volume in the liposomes.

In addition, the aqueous medium may contain soluble protective agents, such as chelating agents, which reduce oxidative lipid hydrolysis, or drug degradative effects which may occur on storage, and other pharmaceutically acceptable excipients and additives.

The invention is applicable, more broadly, also to all lipid soluble compounds such as steroids, beclomethansone, dexamethasone, aldosterone, bethamethasone, cloprednol, cortisone, cortivazol, deoxycortone, desoinide, dexamethasone, estrogens, difluorocortolone, fluclorolone, fluorocortisone, flumethansone, flunisolide, fluocinolone, fluocinonide, fluorocortonoline, fluorometholone, flurandrenolone, halcinonide, hydrocortisone, meprednisone, methylprednisolone, paramethasone, prednisolone, prednisone, triaminicinolone, testosterone or their respective pharmaceutically acceptable salts of esters.

Lipid soluble compounds are dissolved in the phospholipid mixture forming the film in the concentration which is desired in the encapsulated in the LUVs. Then the procedure is continued as described above, i.e. preparing the film, drying it, etc., followed by adding the aqueous medium with or without drug to the film and subsequent LUVs formation. Similarly, the combination of lipid soluble and water soluble drug can be conveniently encapsulated in these LUVs by adding the lipid soluble drug to the phospholipids before film formation, forming the film, drying and adding the aqueous solution with dissolved water soluble drug.

The following examples are intended to illustrate this invention and are not to be interpreted to limit it in any way.

EXAMPLE 1

Preparation of Homogeneous LUVs using a Micropatterned Surface of Silicon Wafer

Etched silicon wafer was prepared by the means used in microelectronic industry according to Example 5 and 6. The bottom of the Erlenmeyer flask was cut out and the wafer was glued to the remaining upper part of the flask.

0.5 mg of egg yolk lecithin (EYL) was doped with 3 wt. % of cationic detergent CTAB by dissolving EYL in the mixture of $CHCl_3/CH_3OH$ and mixing it with CTAB in $CHCl_3$, volumetrically, in amount of 50 ul of EYL solution (10 mg/ml) and 15 ul of CTAB solution (1 mg/ml). 5 ml of $CHCl_3$ were added and the mixture was applied on the surface of the wafer at the bottom of the flask. The phospholipid/detergent/solvent mixture was dried by the evaporation of solvent under reduced pressure of approximately 600 mm Hg, at temperature of 20° C., very slowly in the still flask, without any shaking or rotation.

When the organic solvent completely evaporated, the flask was put under vacuum ($10^{-2-3}$ mm Hg) overnight. Then, 1 ml of distilled water was added and on resuspending, LUVs with homogeneous sizes of 1 um were formed. Size was controlled by the sizes of the micropatterned texture (i.e., surface topography) of the template design prepared according to Example 5.

Homogeneity and the size of obtained LUVs was checked by freeze fracture electron microscopy which showed that LUVs were of uniform size of 1 micron and that no MLVs or SUVs or any other particles were present.

By several time repetition, the same size and homogeneity LUVs population was obtained.

EXAMPLE 2

Preparation of LUVs using a Micropatterned Surface of Silicon Wafer

The silicon wafer with the sizes of the micropatterned texture, which characterize its surface topography, being 1 micron, was prepared according to Example 5, and attached to Erlenmeyer flask according to Example 1.

0.5 mg of egg yolk lecithin (EYL) was doped with 3 wt. % of cationic detergent CTAB by dissolving EYL in the mixture of $CHCl_3/CH_3OH$ and mixing it with CTAB in $CHCl_3$, volumetrically, in amount of 50 ul of EYL solution (10 mg/ml) and 15 ul of CTAB solution (1 mg/ml). 5 ml of $CHCl_3$ were added and the mixture was applied on the silicon wafer at the bottom of the flask. The phospholipid/detergent/solvent mixture was dried by the evaporation of solvent under reduced pressure of approximately 600 mm Hg, at 20° C. temperature, of very slowly and without shaking or rotation.

When the organic solvent completely evaporated, the flask was put under vacuum ($10^{-2-3}$ mm Hg) overnight. Then, 1 ml of distilled water with 500 mg of dissolved naproxen was added and on resuspending, LUVs with homogeneous sizes of 1 um were formed. The resulting naproxen-containing LUVs had substantially uniform size, of 1 micron. There was no contamination of the preparation with MLVs or SUVs.

The same procedure was repeated with the wafer put on the bottom of the Petri dish. Again, the same results were obtained with lipids dried on the wafer and subsequent hydration in a Petri dish.

EXAMPLE 3

Preparation Of Homogeneous LUVs With Encapsulated Lipid Soluble Drug

The wafer was prepared according to Examples 5. The flask was prepared as in Example 1.

The mixture of 0.5 mg of phosphatidylglycerol and phosphatidylchloine (molar ratio 3/7) was dissolved in 5 ml of $CHCl_3$ and 300 mg of beclomethansone propionate was added. The mixture was added to the flask having micropatterned surface template bottom. The solvent was evaporated and dried as in Example 1.

When the organic solvent completely evaporated, the flask was put under vacuum ($10^{-2-3}$ mm Hg) overnight. Then, 1 ml of distilled water was added and on resuspending, LUVs with homogeneous sizes of 1 um were formed. Size was controlled by the sizes of the micropattern on the surface topography of the template design prepared according to Example 5.

Homogeneity and the size of obtained LUVs was checked by freeze fracture electron microscopy which showed that LUVs were of uniform size of 1 micron and that no MLVs or SUVs or any other particles were present.

The size, and homogeneity was determined by methods described in Example 1 and showed LUVs of predominant size around 1 micron.

EXAMPLE 4

Preparation Of Homogeneous LUVs From Charged Phospholipids With Encapsulated Lipid and Water Soluble Drugs The used wafer was prepared according to Example 5.

0.5 mg of phosphatidylcholine (PC) was dissolved in 5 ml of $CHCl_3$ and 300 mg of hydrocortisone was added. The mixture was carefully placed on the wafer and the wafer was placed in the spinner and spinned for 10 minutes at 1,000 rpm. The wafer was then transferred to the Petri dish. The mixture was evaporated and dried under the same conditions as used in Example 1.

500 mg of naproxen as dissolved in 1 ml of distilled water. This aqueous medium mixture was added to the phospholipid film and upon resuspending, LUVs were formed with encapsulated hydrocortisone naproxen combination.

The resulting liposomes with encapsulated mixture of lipid soluble nydrocortisone and water soluble naproxen were LUVs of substantially the same size around 1 micron.

EXAMPLE 5

Silicone Wafer Preparation

The following procedure describes the preparation of the micropatterned silicon/silicon dioxide surface on silicon wafer.

Starting material for preparation of the wafer template is silicon wafer. Single crystal wafer, 4" diameter, 20 mils thick, (100) crystal orientation, lightly doped with N type dopant atom: phosphorus; resistivity 20–40 ohm cm was made.

Silicon wafer was first cleaned using $H_2O_2/H_2SO_4$ as a cleaning solution at a temperature of 125° C. for 10 minutes. The water was rinsed in deionized water, dip etched in 10/1 $H_2O/HF$ etchant for 10 seconds and followed by the repetition of the deionized water rinse. Silicon oxidation was used to form an uniform layer of silicon dioxide. Oxidation temperature was 950° C., with an ambient gas $H_2/O_2(2/1)$ for five hours.

Micromasking or transfer of micropattern into polymer material on the wafer was done by spinning photoresist, baking photoresist, exposure, developing, and baking, according to methods used in the semiconductor industry.

Micropatterning of the wafer was done by etching off the exposed layer of silicon dioxide. Plasma etching was performed using gas $C_2F_6/CHF_366/He$ mixture. Afterwards, photoresist was removed from the wafer.

Silicon doping was done by ion implantation using boron as a doping atom, at dose $2.10^{14}/cm^2$, at energy 100 KeV. It was followed by was wafer dopant activation at 1,000° C. for 1 hour using gas $N_2/O_2$. Silicon dioxide etching was done with Etchant $NH_4F/HF$ 6/1 for 1 minute followed by deionized water rinse.

EXAMPLE 6

Alternate Method of Silicon Water Preparation

The same or similar preparation techniques is applied for preparation of bare silicon wafer or the micropatterned substrate with different film types or different substrate material.

Silicon material of different type, orientation, resistivity and sensitivity, is used. These materials are doped in the same way as described in Example 5. In this manner, silicon dioxide, silicon nitride, aluminum, gold, tantalum nitride, are all prepared according to Example 5.

The thickness of thin film material or the depth of micropatterning depends on the material and is from 0.1 um to several microns.

The mask is designed by means of suitable CAD equipment and the micropattern is optically transferred on the chrome photoplate which is subsequently developed and etched. The final mask is a glass plate with chrome pattern. The mask is used as a template to transfer the pattern on the substrate.

What is claimed is:

1. A method of forming a homogeneous population of large unilamellar vesicles comprising:
   preparing a phospholipid composition comprising charged phospholipids, or a mixture of neutral phospholipids and charged phospholipids, or a mixture of neutral phospholipids and a surfactant, with a solvent effective to dissolve the phospholipids;
   depositing the composition onto a micropatterned template support surface to form a film;
   drying the film; and
   adding an aqueous medium to form large unilamellar vesicles of substantially uniform size.

2. The method of claim 1, wherein said depositing is accomplished by evaporation of the solvent and vacuum drying of said support surface.

3. The method of claim 1, wherein said depositing is accomplished by applying the phospholipid/solvent mixture to the support surface and spinning said support surface.

4. The method of claim 2, wherein said support is a wafer bottomed flask, and said wafer is made of silicon and has a micropatterned template surface.

5. The method of claim 1, wherein said aqueous medium has a pH of between about 6 and 7.5

6. The method of claim 1, wherein said aqueous medium contains a water-soluble agent.

7. The method of claim 6, wherein the water-soluble agent is a pharmaceutical agent.

8. The method of claim 6, wherein the water-soluble agent is a chelating agent.

9. The method of claim 1, wherein the phospholipids are selected from the group consisting of: phosphatidylcholine, phosphatidylglycerol, phosphatidylethanolamine, phosphatidylserine, phosphatidylinositol, phosphatidic acid, and cardiolipin.

10. The method of claim 5, wherein the phospholipid is a neutral phospholipid and said phospholipid is mixed with a charged lipid-soluble compound.

11. The method of claim 10, wherein the lipid soluble compound is a charged phospholipid.

12. The method of claim 10, wherein the lipid soluble compound is a charged detergent present at about 1.0–5.0 weight percent.

13. The method of claim 12, wherein the charged detergent is cetyltrimethylammonium bromide.

14. The method as claim 10, wherein the neutral phospholipid is egg yolk lecithin and the charged lipid soluble compound is cetyltrimethylammonium bromide.

15. The method of claim 1 wherein said combining includes the addition of a lipid-soluble pharmaceutical agent.

16. The method of claim 1, wherein the templated support surface is made of silicon, and where said support surface has an etched micropattern having vertical depth dimensions in the range of about 0.1 to 1.0 um and horizontal pattern dimensions in the range of 3–10 um.

* * * * *